US00PP27577P3

(12) United States Plant Patent
Gruber-Genetti et al.

(10) Patent No.: US PP27,577 P3
(45) Date of Patent: Jan. 24, 2017

(54) APPLE TREE NAMED 'GALA SCHNICO RED'

(50) Latin Name: ***Malus domestica* Borkh**
Varietal Denomination: Gala Schnico Red

(71) Applicant: Schniga GmbH, Bozen (IT)

(72) Inventors: Andreas Gruber-Genetti, Lana/Vollan (IT); Thomas Braun, Girlan (IT); Walter Malleier, Lana/Vollan (IT)

(73) Assignee: Schniga GmbH, Bozen (IT)

( * ) Notice: Subject to any disclaimer, the term of this patent is extended or adjusted under 35 U.S.C. 154(b) by 65 days.

(21) Appl. No.: 14/120,597

(22) Filed: Jun. 6, 2014

(65) Prior Publication Data

US 2014/0366231 P1 Dec. 11, 2014

(30) Foreign Application Priority Data

Jun. 6, 2013 (EP) ..... 2013/1524

(51) Int. Cl.
*A01H 5/08* (2006.01)

(52) U.S. Cl.
USPC ..... Plt./162
CPC ..... *A01H 5/0875* (2013.01)

(58) Field of Classification Search
USPC ..... Plt./162
See application file for complete search history.

*Primary Examiner* — Keith Robinson
(74) *Attorney, Agent, or Firm* — Myers Bigel, P.A.

(57) ABSTRACT

*Malus domestica* Borkh 'Gala Schnico Red' variety is distinguished by a unique combination of characteristics including an intensive red overcolor covering 100% of the fruit skin and a 30% higher number of lenticels per unit area on the fruit skin.

3 Drawing Sheets

Latin name of the genus and species: The Latin name of the genus and species of the plant variety disclosed herein is *Malus domestica* Borkh.

Variety denomination: The inventive cultivar of *Malus domestica* Borkh disclosed herein has been given the varietal denomination 'Gala Schnico Red'.

RELATED APPLICATION INFORMATION

This application claims priority under 35 U.S. §119(a) to European Union Community Plant Variety Breeder's Rights Application No. 2013/1524, filed Jun. 6, 2013; the disclosure of which is incorporated herein by reference in its entirety.

BACKGROUND OF THE INVENTION

The present invention relates to a new and distinct Gala variety of apple trees named 'Gala Schnico Red'. The new variety was discovered as a mutation on a Gala plant cultivar 'Schnitzer Schniga' in a cultivated field at 30904 Nals (BZ) Aniage Knoll, Italy.

'Gala Schnico Red' has been asexually propagated by grafting and all the trees of 'Gala Schnico Red' have been observed to remain true to type over successive asexually propagated generations and maintain their unique characteristics.

SUMMARY OF THE INVENTION

The new variety 'Gala Schnico Red' is distinguished from 'Gala Schnico', a comparator variety, by the following unique characteristics of an intensive red over colour covering 100% of the fruit skin as compared 'Gala Schnico', which has an intensive red over colour covering only 80-90% of the fruit skin. In addition, 'Gala Schnico Red' has a 30% higher number of lenticels per unit area on the fruit skin as compared to 'Gala Schnico'.

Asexual reproduction of this new variety by grafting onto rootstock shows that the foregoing and all other characteristics and distinctions remain true to type over successive asexually propagated generations.

BRIEF DESCRIPTION OF THE DRAWINGS

The colours of these illustrations may vary with lighting conditions and, therefore, colour characteristics of this new variety should be determined with reference to the observations described herein, rather than from these illustrations alone.

DETAILED BOTANICAL DESCRIPTION

Figure 1:
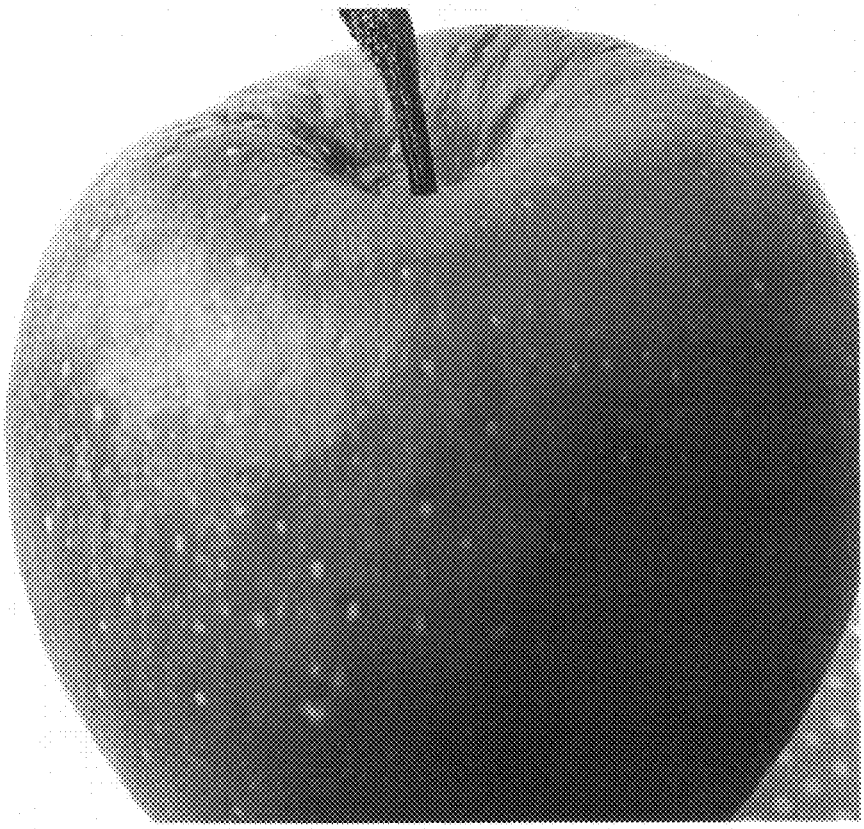
FIG. 1 shows a fruit of 'Gala Schnico Red' from a three-year old tree.
Figure 2:
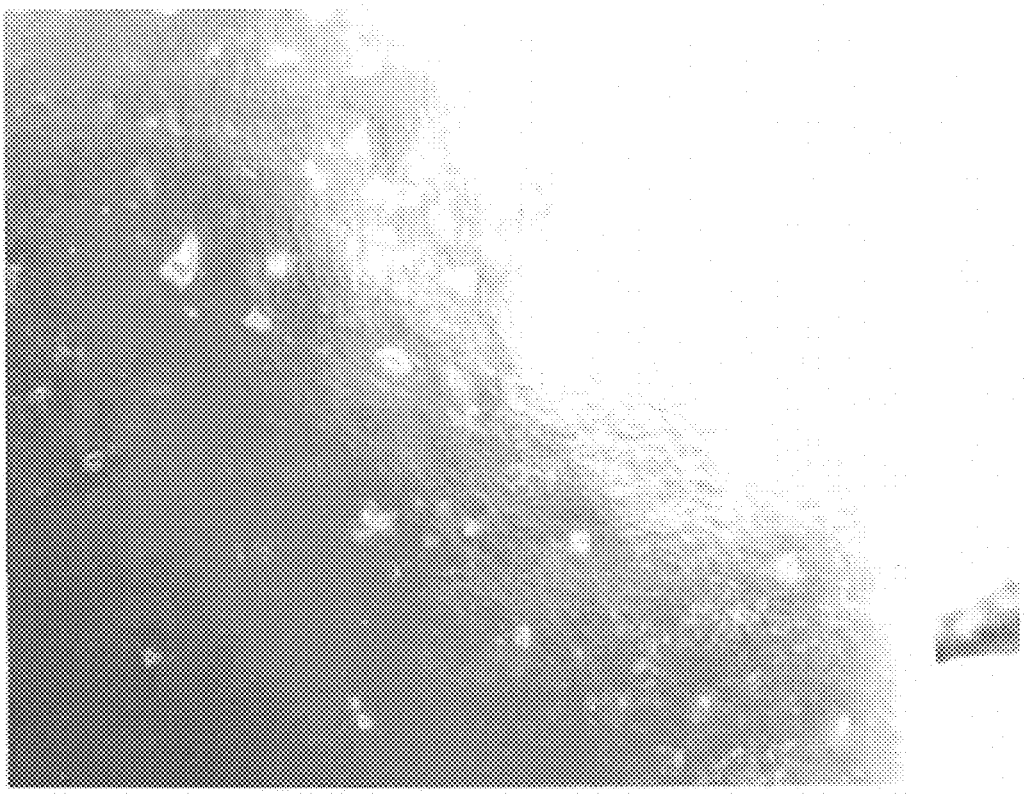
FIG. 2 provides a closer view of the fruit from a three-year old tree of 'Gala Schnico Red' showing the lenticels.
Figure 3:
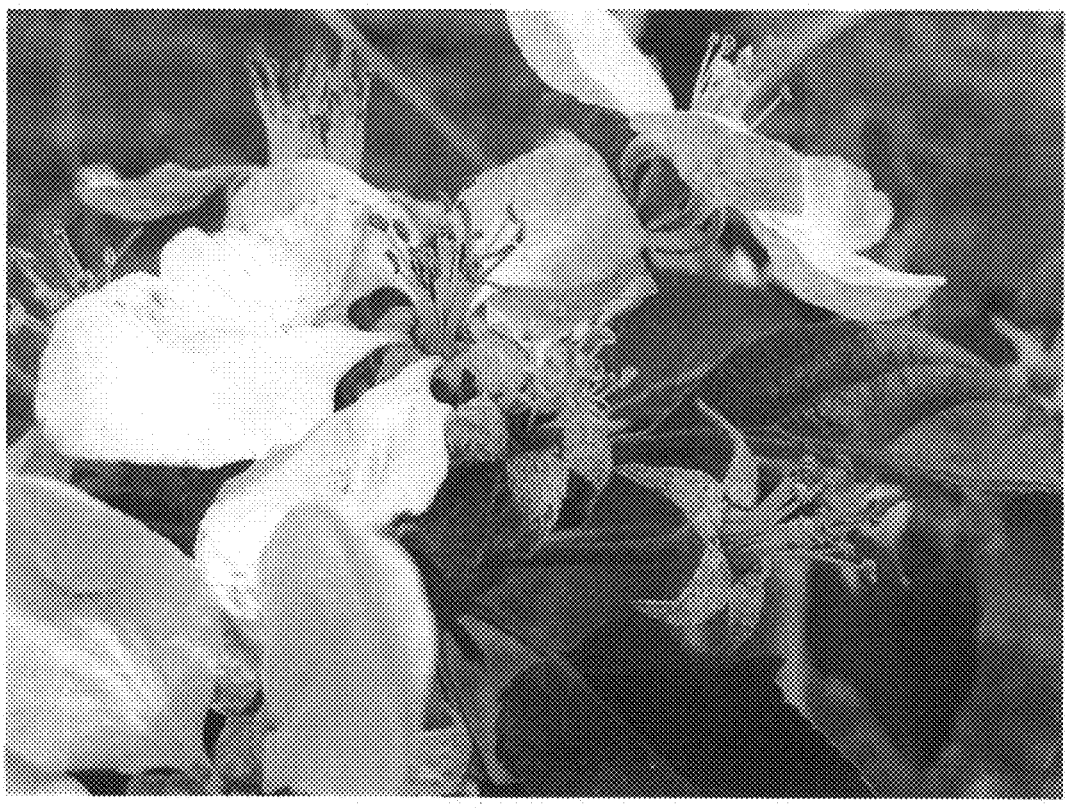
FIGS. 3 shows the flowers of 'Gala Schnico Red' from a three-year old tree.

The following is a detailed description of the 'Gala Schnico Red' variety.

Certain characteristics of this variety may change with changing environmental conditions (e.g., light, temperature, moisture), nutrient availability, or other factors. Quantified measurements are expressed as an average of measurements taken from a number of individual plants of the new variety. The measurements of any individual plant, or any group of plants, of the new variety may vary from the stated average. Colour descriptions and other terminology are used in accordance with their ordinary dictionary descriptions, unless the context clearly indicates otherwise. Colour designations are made with reference to the CPVO-TP/14/2—Protocol For Distinctness, Uniformity And Stability Tests—*Malus domestica* Borkh, Apple.

Parentage: 'Gala Schnico Red' variety originated as a mutation of the Gala cultivar 'Schnitzer Schniga' identified in a cultivated field in Aniage Knoll, Italy.

Tree: The trees described here are three years old derived from the vegetatively propagated 'Gala Schnico Red' mutation and grown on rootstock.

Tree type: Ramified; Habit: spreading.

Tree description:

*Height.*—3.2 m.

*Spread.*—At the height of 60 cm.

*Vigor.*—Medium.

Trunk:

*Diameter.*—2-3 cm.

*Texture.*—Smooth to rough, pronounced cells.

*Color.*—Green brownish greyish with marked lenticels.

*Lenticels.*—Marked, red brown color.

*Lenticel size.*—0.5-1.5 mm.

Branches, primary:

*Length.*—60-80 cm.

*Diameter.*—1.5 cm.

*Angle.*—80-90° (flat).

*Color.*—Greyish brown.

Leaves:

*Shape.*—Elliptic.

*Length.*—11-13 cm.

*Width.*—4-5 cm.

*Leaf blade.*—8-10 cm.

*Margins.*—Dentate.

*Shape of apex.*—Acicular.

*Color* (*upper and lower*).—Intense green (upper); light green (lower).

*Texture.*—Hardly haired surface, medium-strength pronounced veins; well pronounced main vain.

*Leaf attitude.*—Upward.

*Petioles.*—Length: 3 cm. Width: 2.5 mm. Color: light green. Texture: hairy.

*Stipule.*—Rudimentary stipules. Shape: eliptical shape. Length: 1-3 mm. Width: 1 mm. Color: light green. Texture: slightly haired surface, strength pronounced main vein.

Inflorescence:

*Petals.*—Shape=inversely heart-shaped to inversely ovoid. Length=0.5-0.8 cm. Apex=0.8 cm. Base=0.4 cm. Margin=smooth. Color (upper and lower surfaces)=white (CPVO/UPOV Nr.19, Note 1) and light pink (upper) (CPVO/UPOV Nr.19, Note 3); white (under) (CPVO/UPOV Nr.19, Note 1). Petal arrangement=overlapping. Number of petals per flower — 5.

*Sepals.*—Quantity: 5 sepals. Shape: conic. Color: green. Size: 5 mm.

*Fragrance of the flower.*—Absent.

Flower buds:

*Length.*—4-5 mm.

*Width.*—1.5-2 mm.

*Shape.*—Round.

*Color.*—Brown scaled.

Reproductive organs:

*Pistil.*—0.5 mm, white.

*Stigma.*—0.2 mm, white yellowish; positioned above or at same level with the anther.

*Style.*—0.3 mm, white.

*Anthers.*—0.1 mm, yellow.

*Filaments.*—1.1 mm, green.

*Ovary.*—0.5 mm, white.

*Amount of pollen.*—Medium.

*Color.*—Yellow.

Seeds:

*Shape.*—Elliptic.

*Length.*—4 mm.

*Width.*—2 mm.

*Texture.*—Smooth surface texture.

*Color.*—Red brown.

*Number of seed per fruit.*—5-10 seeds.

Time of beginning of flowering: Comparable to the apple varieties 'Cox's Orange Pippin' and 'Jonagold'; about March 20 in Verona, Italy.

Fruit: Relative area of overall colour is very large and is comparable to the apple variety 'Red Jonaprince'. The hue of over colour with bloom removed is purple red (CPVO/UPOV Nr.37, Note 4), which is comparable to the apple varieties 'Red Jonaprince' and 'Spartan'. The pattern of over colour is solid flush with weakly defined stripes similar to the apple variety 'Obro Gala'.

*Quantity of fruit per cluster.*—3-5 fruits.

*Diameter.*—65-85 mm.

*Weight.*—200-350 gr.

*Shape.*—Conical.

*Pedicels length.*—2 cm.

*Pedicel diameter.*—1 mm.

*Pedicel color.*—Green.

*Stalk length.*—Long.

*Stalk thickness.*—Medium.

*Stalk width.*—Medium.

*Eye basin depth.*—Shallow.

*Eye basin width.*—Broad.

*Greasiness of the skin.*—Weak to medium.

*Firmness of fruit flesh.*—6,5-7 kg/cm$^2$ (medium).

*Color of fruit flesh.*—Yellowish white (CPVO/UPOV Nr.53, Note 3).

*Flavor of fruit flesh.*—Sweet, refreshing.

*Brix of fruit flesh.*—11-12,5° Brix at harvest.

*Acidity of fruit flesh.*—3.5-4.5 g/l malic acid at harvest.

*Aroma of fruit flesh.*—Slightly sour.

*Juiciness of fruit flesh.*—Depends on the date of harvesting, thus; when harvested early in the harvesting period the juiciness is stronger and when harvested late, the juiciness is weaker.

Pollination varieties: 'Red Delicious', 'Granny Smith' and 'Golden Delicious'.

Time of eating maturity of fruit: About the beginning of August; comparable to the apple varieties 'Elstar', 'Gala' and 'Honeycrisp'.

Time for harvest: South Europa: about the end of July/beginning of August. North Europa: about the middle of August/end of August.

Drought resistance: Short-term drought resistance; irrigation must be available.

Hardiness: European zone 8.

Comparison of 'Gala Schnico Red' to the parent tree, 'Schnitzer Schniga': The main distinguishing feature between 'Gala Schnico Red' and its parent, 'Schnitzer Schniga' is the intensity of the apple color. The fruit of the variety 'Gala Schnico Red' is very intense (100%) and especially suitable for areas without a good environment for the development of the fruit coloration. 'Schnitzer Schniga' is half intensive. about 50%—(depending on its location) and it is suitable for regions with good environmental conditions for the development of the fruit coloration. In addition, 'Gala Schnico Red' apple has 30% more lenticels than 'Schnitzer Schniga' and the coloring of the 'Gala Schnico Red' apples starts very early, much earlier than the beginning of the coloring of the 'Schnitzer Schniga' apples. The flowering of these two varieties is very similar. Finally, the growth, branch, trunk, and leaves of these two varieties are similar.

Disease and insect/pest resistance: No significant disease or insect pest has been observed to date.

What is claimed is:

1. A new and distinct cultivar of *Malus domestica* Borkh named 'Gala Schnico Red', substantially as illustrated and described herein.

* * * * *